United States Patent [19]

Pawlak

[11] 4,263,914

[45] Apr. 28, 1981

[54] REUSABLE SUPPOSITORY HEMORRHOID DILATOR

[76] Inventor: Edward S. Pawlak, 5437 State Rd., Parma, Ohio 44134

[21] Appl. No.: 971,025

[22] Filed: Dec. 19, 1978

[51] Int. Cl.³ .................... A61M 29/00; A61M 7/00; A61F 5/00

[52] U.S. Cl. .................... 128/341; 128/56; 128/67; 128/79

[58] Field of Search .................... 128/341, 79, 56, 61, 128/67

[56] References Cited

U.S. PATENT DOCUMENTS

| | | | |
|---|---|---|---|
| 115,285 | 4/1871 | Dithridge | 128/341 |
| 1,040,404 | 10/1912 | Poindexter | 128/341 |
| 1,042,624 | 10/1912 | Wagoner | 128/341 |
| 1,149,971 | 10/1914 | Wagoner | 128/341 |
| 1,327,786 | 1/1920 | Stephan | 128/341 |
| 1,573,693 | 2/1926 | Engstrom | 128/67 |
| 1,928,893 | 10/1933 | Hoard | 128/341 |
| 2,074,735 | 3/1937 | Puttcamp | 128/67 |
| 2,153,753 | 4/1939 | Hayton | 128/341 |
| 2,408,860 | 10/1946 | Lindblad | 128/67 |
| 2,631,586 | 3/1953 | Reilly | 128/341 |
| 2,711,172 | 6/1955 | Booth | 128/261 |
| 3,894,539 | 7/1975 | Tallent | 128/341 |

FOREIGN PATENT DOCUMENTS

| | | | |
|---|---|---|---|
| 970237 | of 1975 | Canada | 128/341 |

*Primary Examiner*—Robert W. Michell
*Assistant Examiner*—C. W. Shedd
*Attorney, Agent, or Firm*—John M. Romanchik, Jr.

[57] ABSTRACT

A suppository device for insertion into the rectum in order to provide relief from hemorrhoids; the device including a cylindrical shaft made of plastic, a forward end being rounded, ovate, enlarged and elliptical in cross section, a rear end having an enlarged disk-shaped flange, and a narrow opening longitudinally completely therethrough; the device is adapted for rotational massaging.

1 Claim, 5 Drawing Figures

REUSABLE SUPPOSITORY HEMORRHOID DILATOR

This invention relates generally to suppository devices.

A principal object of the present invention is to provide a dilating device for insertion into the rectum, which gives relief and promotes blood circulation to vital areas, such as both sphincter muscles, including the plexus, (nerves and vessels), thereby contributing to relaxation and deeper breathing and overcoming tension and anxiety, which are a major cause of hemorrhoids.

Another object is to provide a suppository hemorrhoid dilator, that is reusable, and which eliminates the necessity of continued use of dissolvable suppositories.

Other objects are to provide a reusable suppository hemorrhoid dilator, which is simple in design, inexpensive to manufacture, rugged in construction, easy to use and efficient in operation.

These, and other objects, will be readily evident upon a study of the following specification, and the accompanying drawing, wherein.

Figure 1:
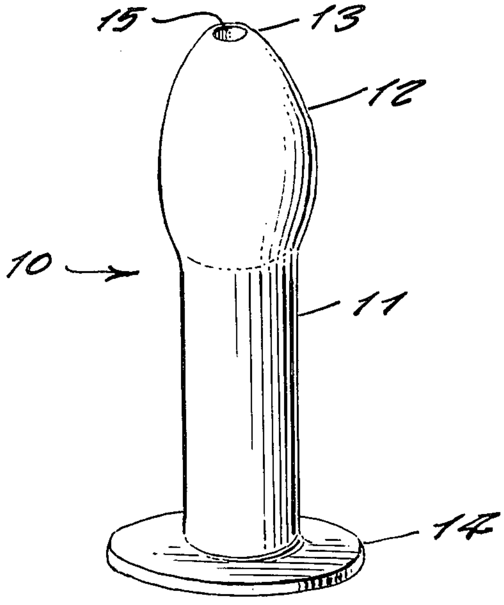
FIG. 1 is a perspective view of the present invention.
Figure 2:
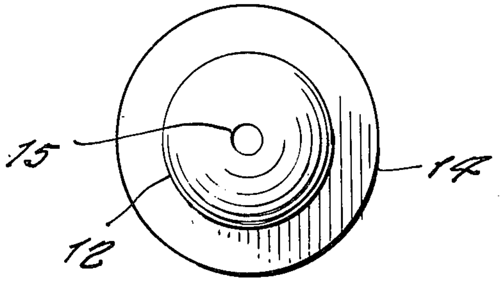
FIG. 2 is a top plan view thereof.
Figure 3:
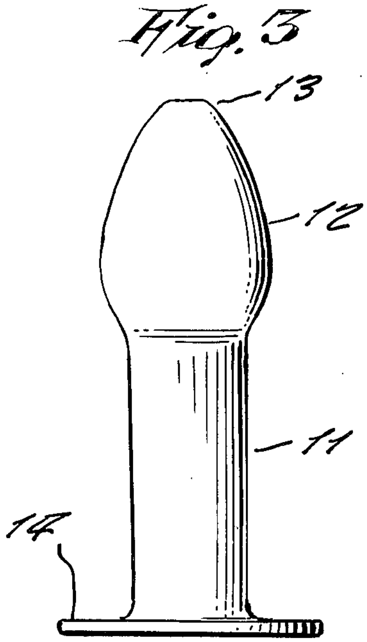
FIG. 3 is a side elevational view.

Referring now to the drawing in greater detail, and more particularly to FIGS. 1 through 4 thereof, at this time, the reference numeral 10 represents a reusable suppository hemorrhoid dilator, according to the present invention, wherein the same comprises a single member made of a medically approved plastic as taught by U.S. Pat. No. 3,894,539, and which includes an elongated, cylindrical shaft 11, which at one end, has a diametrically enlarged rounded ovate-shaped head 12 that tapers eliptically, gradually, to an end 13. An opposite base end of the shaft has a diametrically enlarged, relatively thin, flange 14. A longitudinal opening 15, of small size, extends axially through the shaft and head.

The patient is given the following general directions for the use of the dilator:

The dilator should be warmed by immersing in warm water for a few minutes, removed, dried and the outside of the form well lubricated with vaseline for easy insertion.

In starting a course of treatment, always begin with the smallest dilator. When this can be inserted without undue sphincter resistance, proceed with the next size. When using the larger ones, first insert and withdraw the small form several times. This procedure should be followed as one progress to the larger form.

In the event one have difficulty inserting the dilators, even the smallest one, try the following methods: If one severe hemorrhoids, a "sitz bath"is helpful. This means sitting in a bathtub filled with water as hot as you can stand for five to ten minutes. The water should only cover the rectum and thighs. For the milder case of hemorrhoids, wet a small towel or even a wash cloth with hot water and place on the rectum for a few minutes. The towel cools quickly so repeat this procedure several times immediately. The purpose of both of these instructions is to relax one and motivate the anus muscle to also become relaxed making the introduction of the dilators a little easier.

After lubrication, one can squat, or rest one buttock on the edge of the toilet seat when inserting the dilator. Should one choose sitting on the edge of the toilet seat, make sure the lid is down so as not to lose your dilator inside the toilet. When inserted, one can gently sit on one buttock and hold the dilator in place for two or three minutes.

If one prefer one may try the following method: After lubricating, lie on your side, knees flexed, and place the tip or point of the form on the anus and with gentle pressure turn or rotate the instrument. The dilator is inserted as far as its base, and then held in place for a minute. The anal muscle will grasp and hold it in position. Allow to remain for a few minutes or up to one-half hour; slowly remove.

The dilator may be used at any convenient time. However, their use will tend to promote habit time and if convenient, it is suggested that they be used immediately after breakfast or in the evening before retiring.

Figure 5:
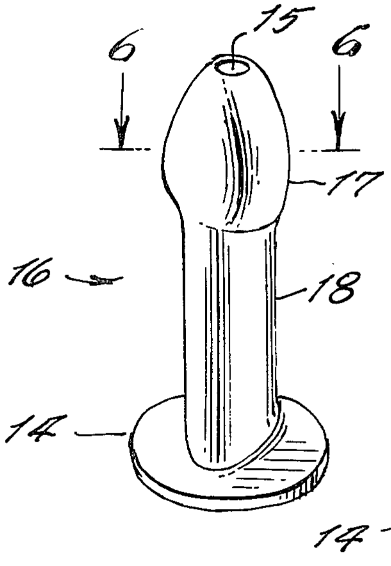
FIG. 5 is a perspective view of a modified form of the invention which has an ellipsoidal head head and ovate shaft having major axes perpendicular to each other so as to be rotatable for massaging purposes after insertion.
Figure 4:
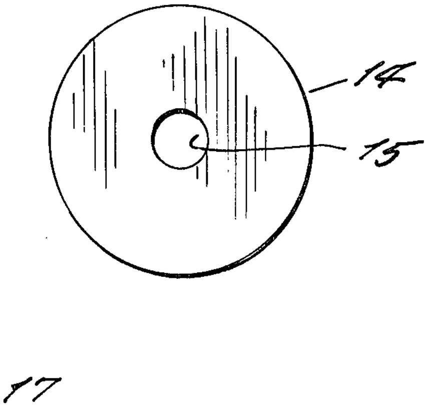
FIG. 4 is a bottom view.
Figure 6:
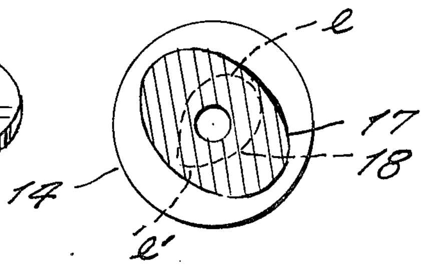
FIG. 6 is a cross-sectional view on line 6—6 of FIG. 5, and showing the ovate instead of the round shape.

Referring now to FIGS. 5 and 6, a modified design of dilator 16 is shown that is generally the same as the above-described dilator 10, except that the head 17 and shaft 18 of the dilator 16 differ by being transversely of elliptical cross-sectional shape, instead of round; the ellipse of the head being at right angle to the ellipse of the shaft when viewed from an axial end, as shown in FIG. 6. Additionally, the ellipse of the shaft is more rounded at one end than at its other end, as indicated at e and e'.

This form of the invention provides an additional massaging action, when the dilator is rotated inside the rectum, due to the elliptical configurations each spreading muscles at the same time on planes at right angles to each other.

While the dilator may be made in any desired dimensions, as preferred by a manufacturer, a practical size is an overall length of three and one-half inches, the major axis of the shaft being three-fourths inch, and the diameter of the flange being one and three-fourths inch.

While various changes may be made in the detail construction, it is understood that such changes will be within the spirit and scope of the present invention as is defined by the appended claims.

What I now claim is:

1. A reusable one piece molded plastic rectal dilator and hemorrhoidal massaging device comprising:

an elongated cylindrical shaft having an ovate cross section;

a disc-like flange at one end of said shaft; when said device is rectally inserted, said flange provides an externally extending gripping means;

an enlarged generally ellipsoidal head molded at the other end of said shaft, the major axis of which head is perpendicular to the major cross sectional axis of said shaft; and a longitudinal opening opening extending completely through said device;

whereby after rectally inserting said head and said shaft; rotating said gripping means causes said ovate and ellipsoidal members to massage body tissue adjacent thereto.

* * * * *